United States Patent [19]
Gerhard

[11] Patent Number: 5,843,008
[45] Date of Patent: Dec. 1, 1998

[54] METHOD FOR MITIGATING PAIN WHEN COUGHING FOLLOWING SURGERY

[76] Inventor: Harvey Gerhard, 416 Mt. Airy Rd., Basking Ridge, N.J. 07920

[21] Appl. No.: 763,553

[22] Filed: Dec. 10, 1996

[51] Int. Cl.[6] .............................. A61F 5/00; A61F 5/37; A47G 9/00
[52] U.S. Cl. .................... 602/5; 602/19; 5/431; 128/96.1; 128/875
[58] Field of Search ................... 602/13, 19, 63; 2/311, 312; 128/99.1, 100.1, 101.1, 102.1; 5/431, 434, 435, 436, 437

[56] References Cited

U.S. PATENT DOCUMENTS

| | | | |
|---|---|---|---|
| 4,294,239 | 10/1981 | Oram et al. | 602/19 X |
| 4,683,601 | 8/1987 | Lagin | 5/431 |
| 4,799,275 | 1/1989 | Sprague, Jr. | 5/431 |
| 4,829,613 | 5/1989 | Yon | 5/431 |
| 5,007,412 | 4/1991 | DeWall | 602/19 |
| 5,445,601 | 8/1995 | Harlow | 602/19 |
| 5,528,771 | 6/1996 | Yudin | 602/19 |
| 5,551,085 | 9/1996 | Leighton | 602/19 X |
| 5,628,721 | 5/1997 | Arnold et al. | |
| 5,692,246 | 12/1997 | Benedick | 2/463 |

*Primary Examiner*—Richard J. Apley
*Assistant Examiner*—Kim M. Lee
*Attorney, Agent, or Firm*—Lerner, David, Littenberg, Krumholz & Mentlik

[57] ABSTRACT

A device and method are provided for mitigating the pain experienced by a patient, after surgery to portions of the patient's torso, when the patient coughs, and for increasing the effectiveness of the patient's cough. The device may include a back portion and two wing portion for compressing a portion of the patient's torso with inward and downward forces. A vest shaped device is also possible. Methods are also described for use of the aforementioned devices.

7 Claims, 11 Drawing Sheets

METHOD FOR MITIGATING PAIN WHEN COUGHING FOLLOWING SURGERY

FIELD OF THE INVENTION

The present invention relates generally to devices and methods for mitigating the pain associated with surgical incisions, and particularly to devices and methods for compressing or constricting at least a portion of a patient's torso to mitigate the post-operative pain associated with surgical incisions, when a patient is coughing, as well as to improve the effectiveness of the patient's coughing.

BACKGROUND OF THE INVENTION

It is vitally important after surgery that a patient continually clear his or her trachea (i.e., airway) of phlegm or mucus to avoid clogging their airway. This clearing is generally accomplished by initiating and completing a cough. A physiological cough is generally initiated by a deep inspiration followed shortly by a forced expiration. The expiratory phase will occur against a closed glottis. This is known as the compressive phase of the cough. After a full inspiration, the thoracic muscles begin to compress the chest in order to provide pressure against the closed glottis. The glottis will then open, allowing for the rapid expiration of airflow. This is known as the expulsive phase of the cough.

As one may readily imagine, a larger lung volume provides for better mechanical efficiency of the expiratory muscles during a cough. This is due, in part, to an improvement in the elastic recoil of the lungs, as well as increased mechanical leverage of the intercostal muscles and ribs. The effectiveness of a cough will depend, to a great degree, on the peak airflow that is generated. The greater the expiratory force of the intercostal muscles and ribs, the higher the peak airflow during a cough. Since the efficiency of a cough in clearing the airway is a function of the velocity of air passing through the airway, the greater the rate of expiratory airflow, the more effective the cough. An effective cough means one which clears a patient's airway of phlegm or mucus.

After a thoracotomy (i.e., surgical incision of the chest) or after surgery in the abdominal area, the mechanics of a normal physiological cough are altered by, inter alia, secondary pain resulting from, in part, surgical incisions. For example, in patients who have undergone surgery involving a sternal incision, as the exparatory phase of a cough begins, the sternum is pulled outward from the center of the torso along its surgical incision site. With the rapid expiration of the cough, the incision site further separates as the patient's muscles contract and rib cage shifts, pulling at the sternum. At about this same time, the diaphragm pushes up toward the lungs and airway, increasing the pressure in the chest. Thus, during a cough, when a deep breath is taken, and as the air is expelled, the interthoracic pressure increases, thereby pulling apart the sternum and causing pain. Further pain, and indeed, injury to the incision site may occur as the cough dissipates and the separated sternum is violently compressed to a resting position.

As a result of the above shifting of parts of the patient's torso, and the resulting pain when coughing, the patient subsequently looses the effectiveness of the cough. That is, because of the severe pain, the patient will tend to take a less than full inspiration during the compressive phase and/or will suppress the urge to cough entirely in an attempt to mitigate the attendant pain. The former results in a related lowering in the exparatory rate of airflow during the expulsive phase and a resulting less-than-desired, inefficient and ineffective physiological cough. The latter results in a clogged airway and related complications. Both result in a medically undesirable situation by reducing the overall effectiveness of the cough, both in terms of efficiency and overall cumulative effect.

If a patient could mitigate the pain experienced when coughing by, for example, containing or compressing the torso, i.e., preventing the outward and upward movement of the chest or abdomen, the patient would be encouraged to cough and to take a fuller and deeper breath when coughing, experiencing a less painful, more efficient and effective cough. As used herein, outward means in a direction generally outward from the sides of the torso (i.e., laterally of the torso) and upward means in a direction generally upward from the back to the chest of the torso (i.e., from posterior the torso to anterior the torso).

Prior attempts at achieving a less painful and more effective cough in this manner include wrapping an elastic bandage around the patient to restrict the outward and upward movement of the affected area of the torso. The bandage applies a continuous inward and downward constraint about the torso, whether or not the patient is coughing. As used herein, inward means in a direction generally inward from the sides of the torso (i.e., medially of the torso) and downward means in a direction generally downward from the chest to the back of the torso (i.e., from anterior the torso to posterior the torso).

An elastic bandage and a method of using same causes continuing, undue and unnecessary discomfort for the patient. Perhaps most importantly, the use of such a wrapped device may be counter-productive. If the wrap is tight enough to help in effective pain mitigation, it will also present a problem in terms of the patient's normal breathing. Such a device would also be uncomfortable to the patient, particularly when used for hours or even days following surgery.

This type of bandage also may lead to dangerous situations for the patient. For instance, if there were a medical emergency and medical personnel needed to access the patient's chest or abdomen quickly, they first would have to unravel the bandage. In certain emergencies, seconds are critical as to whether a patient will survive such an incident. Having to remove the bandage carefully, or even to cut it away, takes precious time from the patient when he or she could be getting immediate treatment. Finally, this type of bandage does not lend itself to easy insertion and removal of tubes, cables and wires or other ancillary components associated with monitoring and life-support and other medical apparatus since there is an absence of defined orifices in which these devices may pass through while the bandage is in place. In addition, a patient must sit upright to allow the bandage to be changed or replaced when cut-away. This may be difficult and painful for the patient.

Another attempt to solve the above problems is to give the patient a pillow to place over the area affected by surgery. According to this approach, when a patient is about to cough, he or she crosses his or her arms over the pillow and applies a downward force to attempt to prevent the affected portion of the torso from expanding upward, separating the incision site and, thus, causing pain. Unlike the bandage type device, this device has the advantage of only applying a compressive force when needed. However, with this apparatus, the patient's torso is still allowed to expand outward during a cough, or even a sneeze. As explained above, this outward movement tends to decrease the effectiveness of the cough. It also causes the patient to experience severe pain since the area affected by surgery is able to expand outwardly, which, in turn, allows the incision site to again separate. Therefore, a patient is still discouraged from coughing deeply or coughing altogether.

This attempted solution also requires the patient's arms to bear the complete brunt of creating the necessary downward force or otherwise act as the compression device itself. Following surgery, a patient may not have sufficient strength to accomplish any amount of meaningful force, rendering the pillow all but useless. In other situations, this type of device may not be used at all. Certain patients may be unable to use one or both arms following surgery, either because of the presence of catheters, separate surgical procedures, or simply because the patient has lost the use of one or both arms. For such patients, the pillow provides no relief at all.

Accordingly, there is a need for devices and methods for mitigating the pain associated with a surgical incision site, when a patient coughs. There also is a need for devices and methods for increasing the effectiveness of a cough. Preferably, at least part of these devices should be easily removable so that medical personnel may attend to the patient most readily. These devices also should be capable of accommodating ancillary components associated with monitoring, life-support or other medical apparatus while such devices are in place and/or in use.

SUMMARY OF THE INVENTION

The present invention addresses these needs. The present invention provides a device for mitigating the pain experienced by a patient during coughing following surgery to at least one portion of a patient's torso. Alternatively, the device may be used for increasing the effectiveness of a patient's cough following surgery. Most preferably, the device will satisfy both objectives at once. A device in accordance with the present invention should meet a number of criteria. It should be comfortable to the patient, easy to use, provide easy access to an incision site located on the torso of the patient during emergencies and provide sufficient compressive force to assist in maintaining a specific configuration of the rib cage during coughing episodes. Specifically, it should help prevent the outward expansion of the chest during a cough and the opening of an incision site. The device must be easy to actuate just before or during a cough and easy to deactuate just following a cough. In fact, the device must be capable of being repeatably and almost instantaneously actuated and deactuated as a patient may cough several times, with brief interruptions, over an extended period of time. Any configuration which can meet these various criteria is contemplated hereby.

One aspect of the present invention provides a device for mitigating the pain experienced by a patient during coughs following surgery to at least one portion of the patient's torso and for increasing the effectiveness of the patient's coughs. The device may include a means for constricting at least the portion of the torso of the patient. It may also include an operating means for actuating the means for constricting so as to apply a compressive force to the torso. This force is directed in a generally inward direction. The operating means is also provided for deactuating the means for constricting to release the compressive force. The device should also be immediately and repeatedly actuable just prior to or during a cough and immediately deactuable immediately following a cough.

In a particularly preferred embodiment the device may further include a first means for modifying the compressive force applied to a region of the torso, and specifically to an incision site on the torso.

In another particularly preferred embodiment of the present invention, the means for constricting is provided with a means for retaining same in a position about the torso of the patient when the patient is standing. This means for retaining, in a combination with the means for constricting, may be provided in the form of, for example, a vest. Of course, any other arrangement which allows for a full range of constriction and which prevents the device from slipping off a patient when the patient sits up or stands is contemplated as well.

In a particularly preferred embodiment in accordance with the present invention, the device for mitigating the pain experienced by a patient during cough following surgery includes a back portion and at least one, and usually a plurality of wing portions which are disposed to be wrapped around the patient's torso. The wing portions may be attached to the back portion or may be integrally formed therewith. Just before coughing, these wings may be grasped such that they crisscross the chest of the patient. When force is applied in an opposing direction as the patient moves his or her arms in an outward and/or downward motion relative to the body while grasping the ends of these wing portions, the device constricts around the patient, thereby restricting the range of movement of the rib cage during coughing. Once a coughing episode has subsided, the device can be deactuated by releasing the wing portions, thereby removing the constrictive action of the device and the compressive force generated thereby.

In accordance with another aspect of the present invention, there is provided a method for mitigating the pain experienced by a patient during coughs following surgery to at least one portion of the patient's torso and for increasing the effectiveness of the patient's coughs. The method includes the step of providing a means for constricting about at least one portion of the torso of the patient. The method also includes the step of causing the means for constricting to constrict about the torso of the patient so as to apply a compressive force to the torso. Again, this force is generally applied in an inward direction. This is all done just prior to, or during, a cough. Finally, the method includes the step of causing the means for constricting to release the compressive force applied to the torso of the patient following the cough.

In a preferred aspect of the present invention, this method may be accomplished by a patient crisscrossing their arms across their chest to grab the ends of opposing wing portions of a device wrapped around at least a portion of their torso. These wings may then be pulled across the body in opposing directions thereby causing a constriction about the torso of the patient as the ends of the opposed wings are pulled across the torso of the patient in opposing directions.

In another preferred embodiment in accordance with the present invention, the method also may include positioning an additional device over the incision site such that an increased compressive force is imparted to the incision site by the constricting means when actuated.

BRIEF DESCRIPTION OF THE DRAWINGS

A more complete appreciation of the subject matter of the present invention and the various advantages thereof may be realized by reference to the following detailed description, where reference is made to the accompanying drawings in which:

FIGS. 4A and 4B are perspective views of another version of a device of the present invention wherein FIG. 4A shows a thick back portion and FIG. 4B shows thick wing portions;

FIG. 5 is a top plan view of another version of the device of FIG. 1 showing means for attaching other material to the device;

DETAILED DESCRIPTION OF THE PREFERRED EMBODIMENTS

Figure 1:
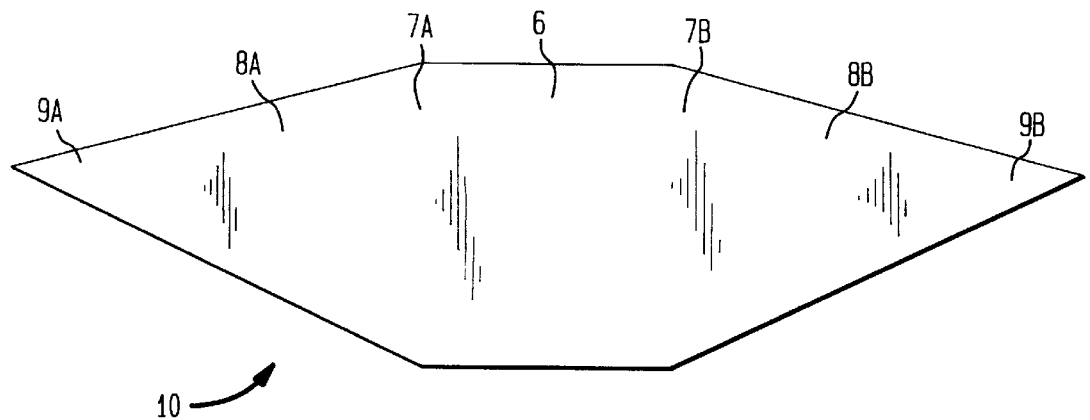
FIG. 1 is a top plan view of one version of a device of the present invention.
Figure 2:
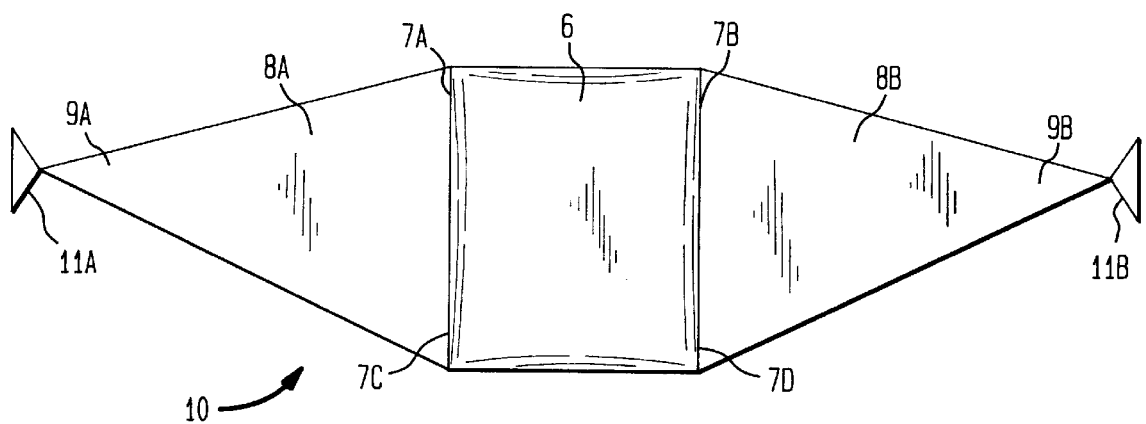
FIG. 2 is a top plan view of the device of FIG. 1 showing defined ends.

Two of the simplest examples of devices in accordance with the present invention are illustrated in FIGS. 1 and 2. The device for mitigating pain 10 illustrated therein is meant to be wrapped around the torso of a patient. Device 10 generally has a section which engages the back of a patient or back portion 6, as well as at least one wing portion. As shown in FIGS. 1 and 2, the device preferably includes a plurality of wing portions 8A and 8B. As shown in FIG. 2, these winged portions, 8A and 8B, can each have a first end, 7A and 7B respectively, and a second end, 9A and 9B respectively. The first ends 7A and 7B are disposed adjacent and are affixed to the back portion 6, while the second ends 9A and 9B are meant to be free and to be wrapped around the torso of the patient. In this embodiment, the first ends 7A and 7B of wing portions 8A and 8B are attached to the edges 7C and 7D of the back portion 6. However, wings 8A and 8B may be attached to any part of back portion 6 as a way of modifying the degree and vector of compressive force applied by each wing portion. In FIG. 1, device 10 is formed from a single sheet of material; therefore, there are no specific seams to delineate the first end portions 7A and 7B of wing portions 8A and 8B, respectively, from back portion 6.

It is not necessary that wings 8A and 8B be tapered as shown in FIGS. 1 and 2. Instead, they may have the same width as back portion 6 or may be even wider.

In general, the device defined by the back portion 6 and the wing portions 8A and 8B constitutes a means for constricting at least one portion of the torso of a patient when actuated. By "constricting," it should be understood that the device in accordance with the present invention generally constricts around the torso as it is pulled around the torso. Often, this will actually cause the constriction of the torso itself. However, that need not be the case. "Means for constricting" in accordance with the present invention also encompasses a structure which itself does not narrow, but which restricts the expansion of the torso during a cough. Thus, a device which can inflate like a blood pressure cuff, and which is placed around a patient's torso to restrict the expansion of the chest and to help prevent the incision site from being pulled apart during a cough, is a constricting device and means for constricting as defined herein. It should also be realized that the chest need not actually be constricted when the device is actuated, although some degree of constriction is good. The device must, however, restrict the expansion of the chest and help prevent the incision site from being pulled apart during a cough.

The device for mitigating the pain experienced by a patient during coughs in accordance with the present invention also comprises means for actuating the means for constricting to cause the means for constricting to constrict around the torso of the patient. Actuation of the means for constricting results in the application of a compressive force to the torso in a generally inward direction. The same operating means for actuating the constricting means also allows for deactuating the means for constricting so as to release the applied compressive force.

As shown in FIG. 1, the operating means for actuating the means for constricting need be nothing more than the second ends 9A and 9B of the means for constricting, i.e., the free ends of wing portions 8A and 8B. These ends may be grasped when a patient crisscrosses their arms across their chest. Then, by pulling the winged portions 8A and 8B across the chest by moving the patient's crisscrossed arms away from the patient's body and/or down to the patient's side, the device 10 is made to constrict around the torso of the patient. This generates a compressive force or forces as previously described.

More preferably, as shown in FIG. 2, the operating means cooperative with the means for constricting is a separate structure such as handles 11A and 11, respectively, which facilitate grasping. The operating means for actuating the means for constricting can be any structure which facilitates constriction of the means for constricting including, without limitation, a handle, a loop, a strap, a pulley system, a recess and the like.

It is not necessary that the operating means for actuating the constricting means be disposed at the second ends 9A and 9B of wing portions 8A and 8B, respectively. Instead, the operating means can be cooperatively disposed anywhere in combination with the means for constricting so long as the proper fit and intermittent constrictive action can be generated on demand.

When the device illustrated in FIG. 2 is used, a patient lies down with back portion 6 engaging their back. Wing portion 8A engages their right side and the second end 9A is loosely resting on their chest or at their sides. Wing portion 8B engages their left side, with the second end 9B also resting loosely on the patient's chest or at their other side. The constricting means which includes the back portion 6 and wing portions 8A and 8B can be actuated by grasping operating means for actuating i.e., handle 11A in a patient's left hand and handle 11B in a patient's right hand. The patient will then move their arms outwardly and/or downwardly such that the wings 8A and 8B are crisscrossed across the body. In short, the wings are drawn toward and past one another, in an almost tourniquet-like manner, about the torso. This action forces the device 10 to constrict about the patient's torso in a tighter and tighter engagement. This, in turn, generates a compressive force generally inward toward the central axis of a patient's torso from substantially all circumferential directions. By either releasing handles 11A and 11B or by re-crisscrossing a patient's arms, the constrictive action of device 10 is reversed thereby relieving the compressive force.

The means for constricting may be produced from a wide variety of materials, including, foams, rubbers, natural fiber containing fabrics, synthetic fiber containing fabrics, mixed fiber blend fabrics, leather, plastic sheet materials and mixtures such as a foam encased in a fabric covering. Preferably, the material will be soft, light, and have some elasticity.

Figure 3:
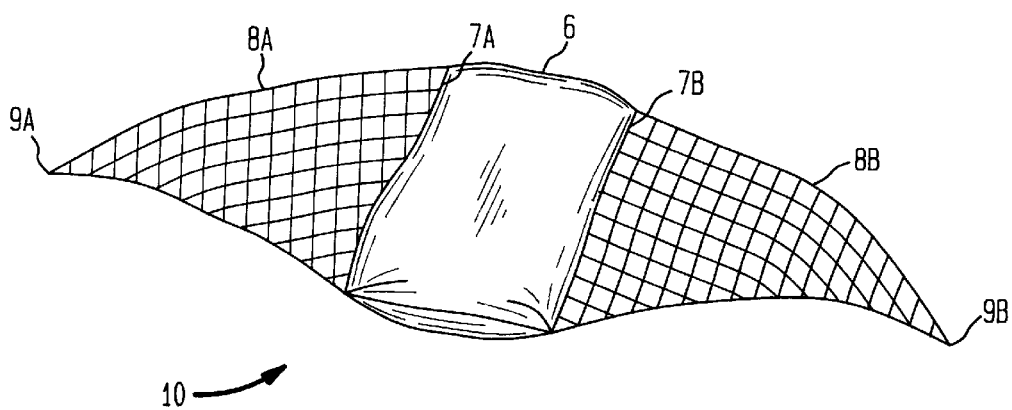
FIG. 3 is a perspective view of another version of a device of the present invention showing netted wings.
Figure 4A:
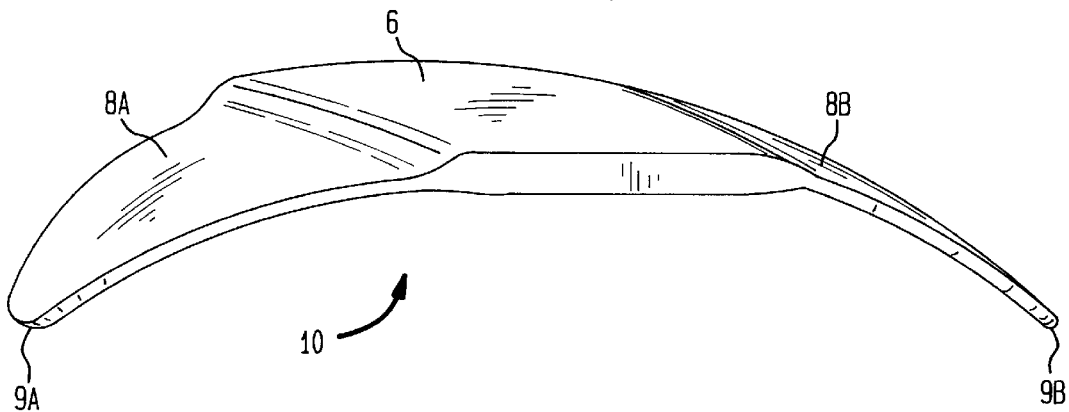
Figure 4B:
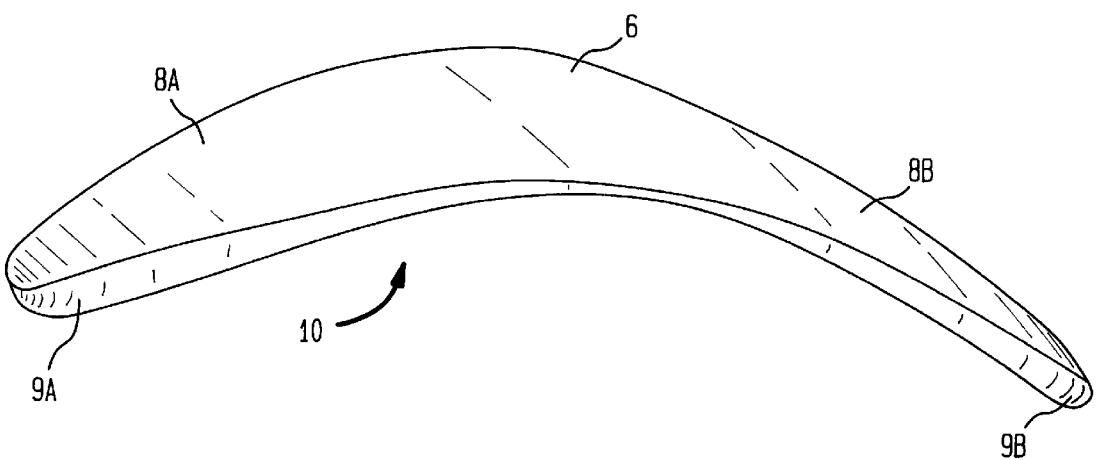

FIG. 3 illustrates the use of a netting material for wings 8A and 8B and a denser woven cloth material for back portion 6. Alternatively, as illustrated in FIGS. 4A and 4B, the means for constricting may be produced from a single piece of material such as a foam. That foam may be covered by a natural or synthetic fabric or can be encased in a polymeric material. Materials such as neoprene, for example, may be used. Furthermore, as illustrated in FIGS. 4A and 4B, the means for constricting may be formed of different thicknesses of material. As shown in FIG. 4A, the back portion 6 comprises a thicker foam than the integrally formed wing portions 8A and 8B. In FIG. 4B, the back portion 6 is formed of a thinner area of foam when compared to the wing portions 8A and 8B.

Figure 5A:
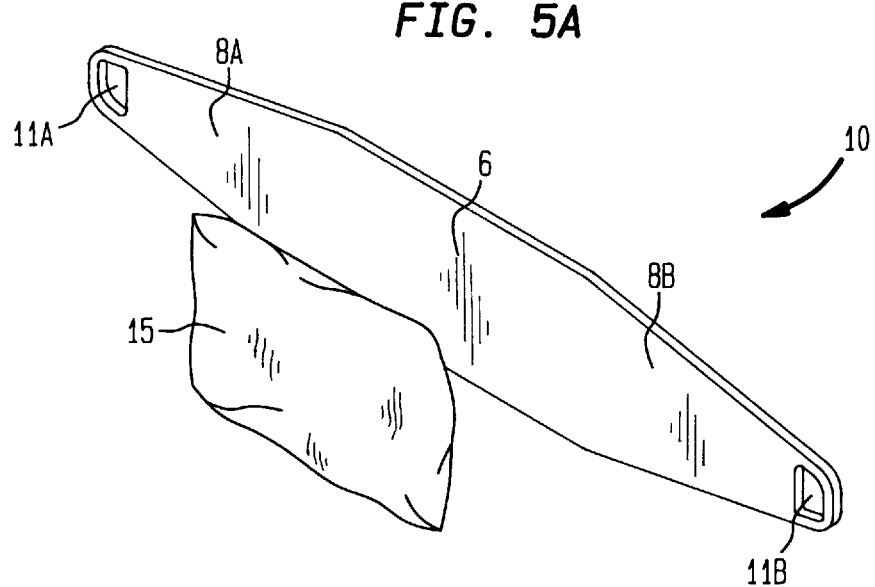
FIG. 5A is a perspective view of another version of a device of the present invention showing the device and an associated pillow.

FIG. 5 illustrates another aspect of the present invention in which a device for mitigating pain as described above also includes a first means for modifying the compressive force applied to an incision site on the torso of the patient. In a preferred embodiment, and as shown in FIG. 5A, this first means for modifying the compressive force is a cushion or a pillow 15 although, it may be a solid object of greater weight and rigidity as well, when it is necessary to apply additional compressive force. Pillow 15 may be manually placed on the chest of the patient and, in particular, over the incision site. The wing portions 8A and 8B of the device illustrated, for example, in FIG. 1 or 5A, may then be draped over the torso as explained previously such that they come to rest on top of the pillow 15. When the device 10 is actuated as previously discussed, it constricts around not only the torso of the patient, but also cushion 15, forcing cushion 15 into the torso of the patient. This may add an additional layer of comfort and may also increase, or depending upon the composition of the first means for modifying the compressive force, decrease the force applied to the torso at the incision site. Cushion 15 may also help distribute the applied compressive force differently.

Figure 6A:
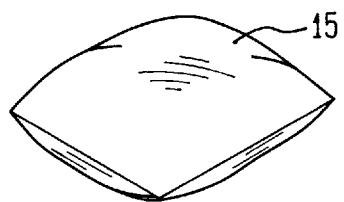
FIGS. 6A, 6B and 6C are perspective views of pillows or cushions to be used with a device of the present invention.
Figure 6B:
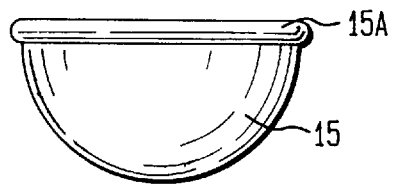

As shown in FIG. 6B, cushion 15 may also include a substantially rigid member made of wood, plastic, metal, masonite or the like, which may be used to further increase the force translated to the incision site. When the constricting device is actuated as previously discussed, the wing portions 8A and 8B will contact the rigid member 15A, which will more efficiently transfer the compressive force to that portion of the torso over which the cushion 15 is placed.

Figure 6C:
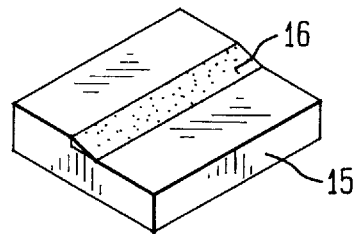

In another embodiment illustrated in FIG. 6C, cushion 15 may be a solitary block of a polymeric foam material to which is affixed a VELCRO® strip 16. VELCRO® strip 16 cooperates with VELCRO® strip 12 disposed on an inner surface of device 10, as illustrated in FIG. 5, to attach and retain cushion 15 in place on wing 8A. Alternatively, cushion 15 could be sewn onto wing 8A or permanently affixed with an adhesive. Finally, cushion 15 could be integrally formed with the second end 9A of wing portion 8A. This wing would appear thicker than the rest of the device 10. See FIG. 4B.

Using this arrangement, the relative position of cushion 15 depends largely upon the placement of VELCRO® strip 12 rather than upon the location of the actual incision site on the patient's torso. Therefore, an alternate arrangement, such as shown in FIG. 5, with reference to wing portion 8B, may be preferable. There, the entire inner surface of at least the wing portion 8B is lined with either VELCRO® or some other material which will cooperate with attaching means 16 to releasably retain same wherever placed. This material is indicated by number 13. This allows the surgeon maximum flexibility in terms of placement of the means for modifying the compressive force applied to the incision site such that it may be disposed to maximize advantage. Of course, while VELCRO® has been disclosed, any other releasable attachment means such as snaps, hooks, non-permanent adhesive and hook and loop materials and the like also may be used.

Figure 7:
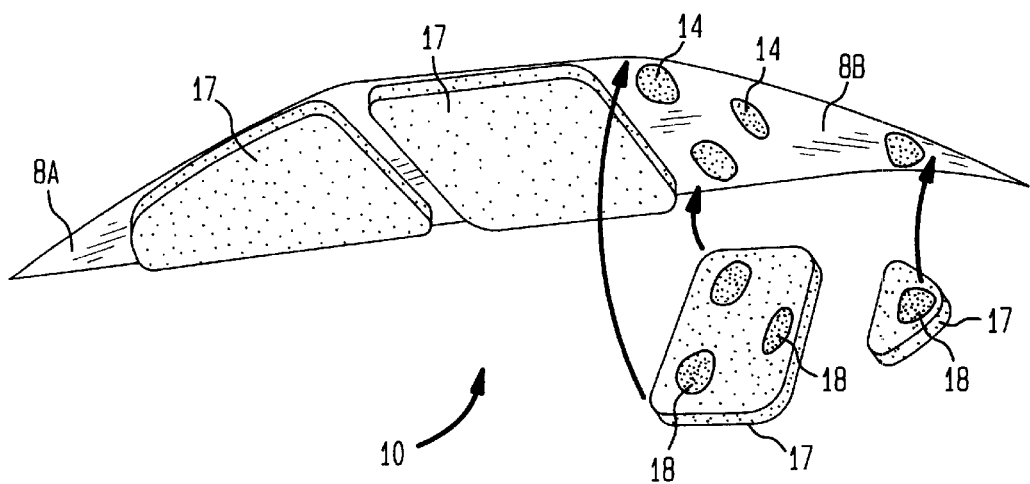
FIG. 7 is a perspective view of the device of FIG. 1 showing associated cushions.

Device 10 may also include at least one second means modifying the compressive force applied to a portion of the torso and/or for adjusting the comfort or fit of the device when the means for constricting is actuated. Unlike the first means for modifying the compressive force, however, this second means for modifying is disposed to engage a portion of the torso of the patient other than the incision site. At the very least, this means will not engage the incision site directly. These second means for modifying therefore may be disposed along wing portions 8A or 8B and/or back portion 6 of device 10. Preferably, these second means for modifying the compressive force applied and/or adjusting the comfort or fit of the device is a cushion or pillow 17 as shown in FIG. 7. Again, this cushion 17 can be an integral part of the means for constricting, as shown by the extra thick back portion 6 in FIG. 4A, or can be attachable or detachable thereto. The device 10 can be provided with one or more VELCRO® patches 14 disposed at various places along the device to receive and releasably attach such cushions 17 which also have been provided with VELCRO® patches 18. Of course, the device 10 may be completely lined on its inner surface with a VELCRO® material or a material to which VELCRO® will stick to allow cushions 17 to be disposed in any desired position.

Figure 8:
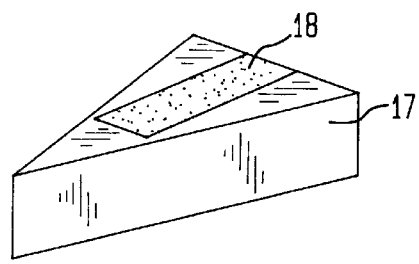
FIG. 8 is a perspective view of a detachably attachable wedge-shaped cushion.

In a particularly preferred embodiment, illustrated in FIG. 8, the second means for modifying the compressive force applied or the comfort of the device 10 thereof is a wedge-shaped cushion 17. Cushion 17 may also include a VELCRO® strip 18 to allow it to engage and be detachably retained by retaining surface 13 on, for example, wing portion 8B and/or the VELCRO® strip or patch 14 disposed on wing portion 8A of the device 10 illustrated in FIG. 5.

The various pillows and cushions 15 and 17 in accordance with the resent invention, as illustrated in FIGS. 6A–6C, 7 and 8, may be made of any material used for such structures. These may include polymeric foams, cloth, beads, feathers such as down, and the like. Similarly, the cushions may be of any size or shape necessary to meet their intended purpose. For example, cushions 17 may be sized and shaped to adjust the fit of device 10 and, therefore, they may be provided in a number of different shapes and thicknesses. Cushion 17, which is intended to be applied to the back portion 6 of a device 10, may be thicker than similar cushions used on wing portions 8A or 8B as, when a patient is lying down, back portion 8 will receive the majority of a patient's weight. Therefore, the greatest amount of cushioning may be required. Alternatively, cushions 17 may be an integral part of device 10, as illustrated in FIGS. 4A and 4B. Finally, a cushion 17 may have a reduced thickness as it is being placed over a portion of device 10 which already has an enhanced thickness. Thus, for example, the device illustrated in FIG. 4A already has additional cushioning 17 built into back portion 6. Therefore, it may require a thinner additional back cushion 17, or no back cushioning at all. The first means for modifying and the second means for modifying also may be an inflatable pillow or a soft-sided bag-like structure containing a liquid or gel. In fact, heating and cooling packs may be used.

Figure 9:
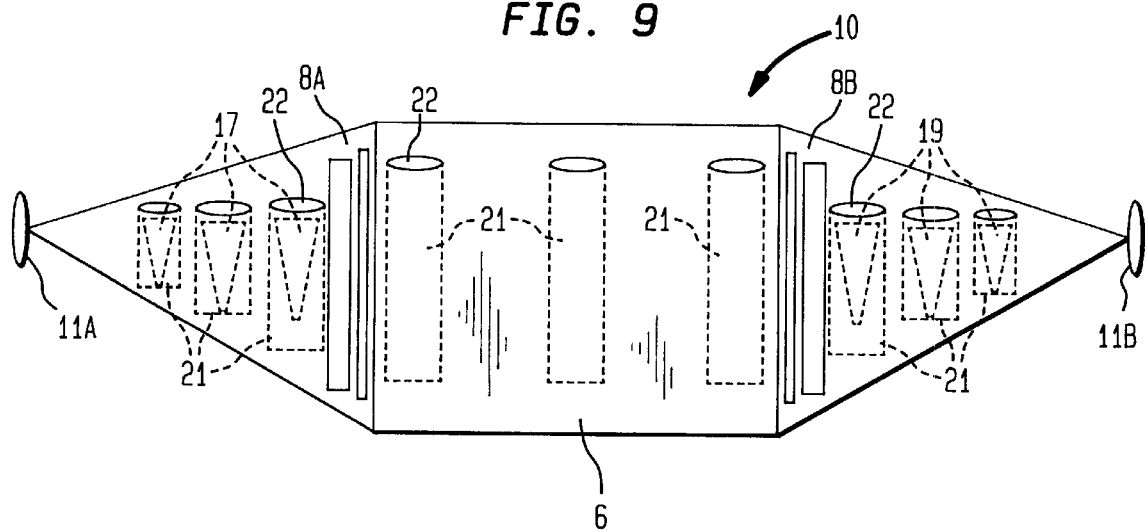
FIG. 9 is a perspective view of the device of FIG. 2 showing additional features.

In an alternate embodiment illustrated in FIG. 9, wings 8A and 8B of device 10, as well as back portion 6 thereof, may be provided with a plurality of cavities 21. These cavities may include access means 22 which may be disposed on either the inside or the outside of device 10. The cavities may also be formed such that they permanently retain their contents and generally no access is provided. As shown in FIG. 9, wing portion 8A includes a plurality of such cavities 21 each of which contains a generally wedged shaped cushion 17. Cushions of any size or shape, of course, may be inserted and retained within cavities 21 to adjust the comfort and fit of the device about the patient's torso as well as to adjust, i.e., increase or lessen, the amount of compressive force applied to that portion of a patient's torso.

Figure 10:
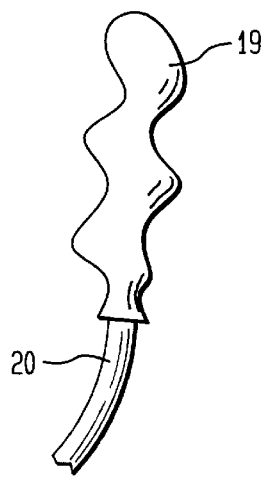
FIG. 10 is a schematic view of a deflated bladder for use with a device of the present invention.
Figure 11:
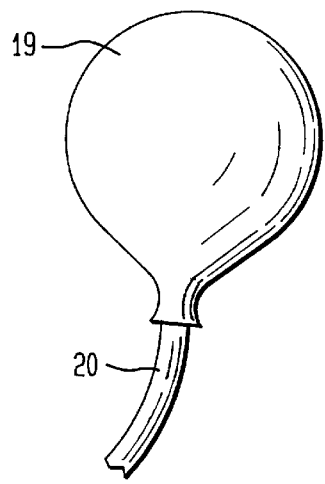
FIG. 11 is a schematic view of the bladder of FIG. 10 when inflated.

Wing portion 8B includes cavities 21 which contain, as a second means for modifying the compressive force applied and/or for adjusting the comfort or fit thereof, bladders 19. A bladder 19 in accordance with the present invention may be a balloon or similar device which may be inflated by fluid or gas from a deflated position, illustrated in FIG. 10 to an inflated position in FIG. 11. This allows for one to adjust the level of compressive force applied with great precision and to modify the degree of compressive force and/or the degree of cushioning provided without having to replace any padding. The means for modifying the compressive force applied to the incision site also may be a bladder arrangement as described herein. Furthermore, bladders 19 need not be inserted into cavities 21. Instead, they may be provided with an attaching means such as a VELCRO® strip 18 such that they may be disposed along the inside of device 10. The bladders 19 also may be a pertinent part of the means for constricting which can be inflated by a pump in the same manner that various sneakers are "pumped up."

In accordance with another embodiment of the present invention, it is desirable to provide a device for mitigating the pain experienced by a patient during coughs after surgery, which can be conveniently used while the patient is in a sitting or standing position. This may be accomplished by the use of a means for retaining the constricting means in a position about the torso of the patient. The means for retaining the constricting means may be something as simple as a plurality of one or more VELCRO® pads/patches placed on an outer surface of a patient's pajama top, gown, or robe. These VELCRO® pads could engage cooperatively placed VELCRO® pads disposed on the inner surface of device 10 or, as shown in FIG. 5 with regard to wing 8B, the entire inner surface of device 10 could be covered with a material which will adhere to a VELCRO® or related material disposed on the patient's garment. Thus, when the patient sits or stands, device 10 is attached to the garment. Of course, under such circumstances, one should ensure that the garment does not include retaining means on the torso area in such a manner which will impede the ability to manipulate the free or second ends 9A and 9B, respectively, of device 10 when 30 actuating the device.

Figure 12:
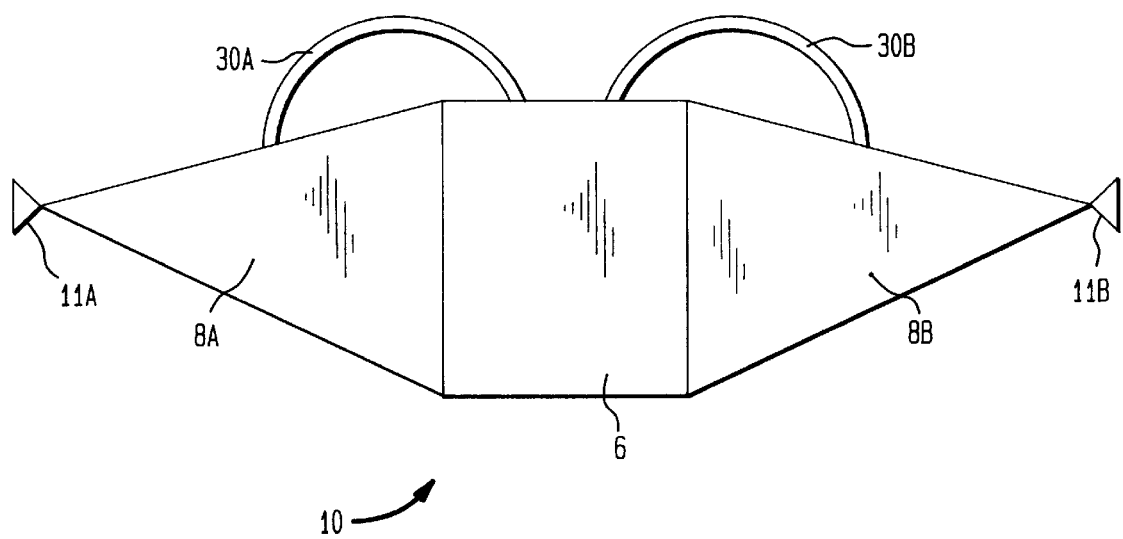
FIG. 12 is a top plan view of the device of FIG. 2 showing straps.

In another embodiment, this goal may be accomplished by a plurality of shoulder straps 30A and 30B connecting the back portion 6 to wing portions 8A and 8B, respectively, as shown in FIG. 12. In this case, a patient lying on back portion 6 would insert their right arm through shoulder strap 30A and their left arm through shoulder strap 30B such that the device 10 will be retained about their torso when sitting or standing. Of course, straps 30A and 30B may be made adjustable or detachable like they are in, for example, luggage straps and the like. It is important that the straps be arranged such that when the device is connected, the shoulder straps do not cause discomfort or injury to the patient's neck or shoulders.

Figure 13:
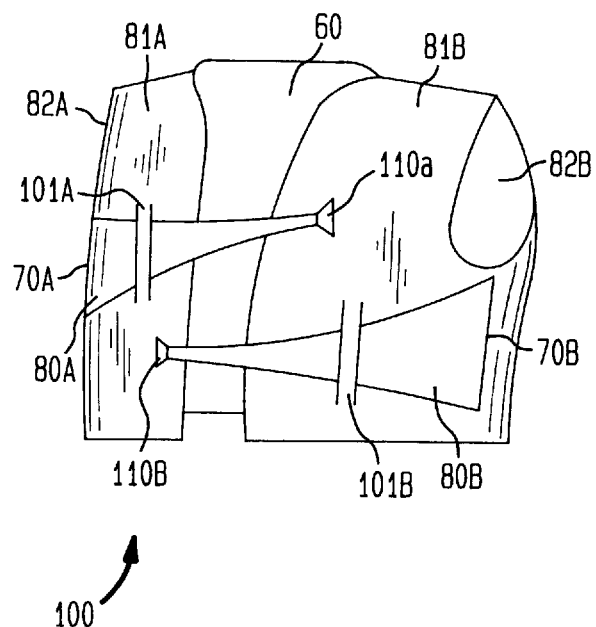
FIG. 13 is a perspective view of another version of the present invention.

An alternative embodiment is illustrated in FIG. 13. In this embodiment, a vest 100 is provided composed of a back panel or back portion 60, a front right panel 81A and a front left panel 81B. The vest is meant to be worn by a patient in a conventional manner, with the right arm fitting through arm hole 82A and the left arm fitting through arm hole 82B. The vest is also provided with a plurality of wing portions 80A and 80B which are permanently affixed at their first ends, 70A and 70B to vest 100. Wing portions 70A and/or 70B may be attached to the back portion 60 or to the front right panel 81A and front left panel 81B, respectively, depending upon the degree and direction of force which is intended to be applied to specific areas of the torso. As should be readily apparent, by adjusting the relative position of the wing portions in this, and in other embodiments discussed herein, one may modify the degree of compressive force applied to various areas of the torso. As illustrated in FIG. 13, however, first ends 70A and 70B of wing portions 80A and 80B, respectively, are attached to the front right panel 81A and front left panel 81B, respectively, under the arm holes 82A and 82B.

When actuated by grabbing operating means for actuating handles 10A and 10B, respectively, in a manner previously described, compressive force is generated by the back panel 60 and by those portions of the front right and front left panels 81A and 81B, respectively, disposed between the junction of the first ends 70A and 70B of wing portions 80A and 80B and back panel 60. Additional compressive force is, as with all of the embodiments previously discussed, generated by the wing portion 80A and 80B. The remainder of front panels 81A and 81B disposed underneath wing portions 80A and 80B, respectively, depending upon their thickness and composition, may or may not modify the compressive force applied during constriction to the chest area. However, these panels generally do not provide compressive force in and of themselves. If made from a semi-rigid material, they may assist in translating the force and spreading the force throughout the area covered thereby.

Device 100 may also be equipped with guides 101A and 101B attached to front panel 81A and 81B, respectively. Wing portions 80A and 80B may be threaded through these guides to ensure that the operating means for actuating 110A and 110B remain in a convenient place such that they may be reached easily by the patient just prior to or during a coughing incident. Of course, any other guide means which can accomplish the same result such as a loop, hook or channel is specifically contemplated hereby. The device of this embodiment, like that shown in FIG. 12, will stay in place and will be actuable by a patient when a patient is in a sitting or standing position as well as when the patient is lying in bed.

In operation, the patient will wear the vest in a conventional manner and, just prior to coughing, would grasp handle 110B with their right hand and grasp handle 110A with their left hand. Then, moving their arms outwardly from the chest and generally toward the side, they would crisscross wing portions 80A and 80B, thereby generating compressive force. They will maintain the pressure by retaining the operating means in the extended position until such time as the cough subsides, at which point they may deactuate the device by letting go of handles 110A and 110B, respectively.

Figure 14:
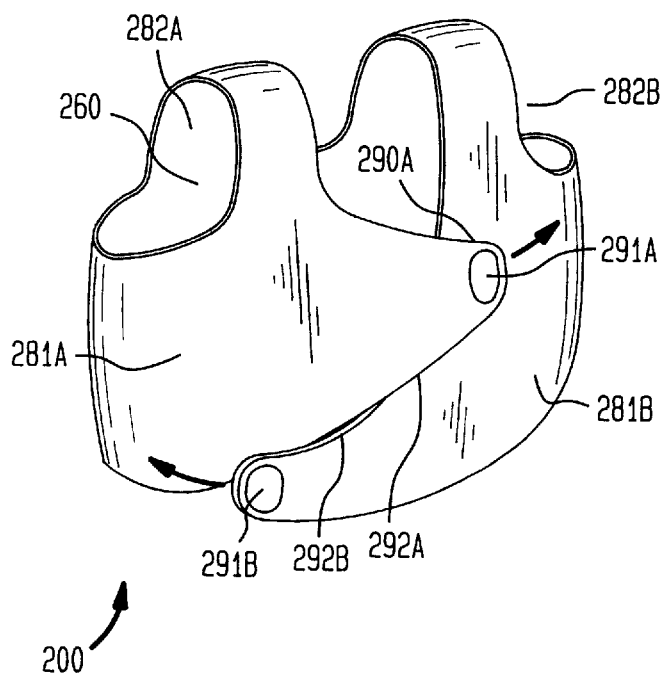
FIG. 14 is a perspective view of another version of the present invention.

As shown in FIG. 14, a vest 200 may be constructed of the back panel 260, a right chest panel 281A, and a left chest panel, 281B. Arm holes 282A and 282B are also provided. In this embodiment, the chest panels 281A and 281B are also the wing portions of the means for constricting. These wing portions 281A and 281B also include, adjacent their second ends, 290A and 290B respectively, apertures or handholes 291A and 291B which act as gripping means or operating means for actuating the means for constricting. The leading edges 292A and 292B are cut away in a cooperative manner as illustrated such that the second ends 290A and 290B can be drawn across the center of the chest without interfering with one another to allow for the creation of compressive force.

The operation of vest 200 is very similar to that of vest 100, illustrated in FIG. 13, and, indeed, all of the prior devices described herein. The device would be worn by a patient immediately as any other vest would be worn. Just prior to or after the beginning of a coughing episode, a patient would actuate the device 200 by grasping the actuating means which, in this case, are the second ends 290A and 290B of wings 281A and 281B, respectively. The patient would grasp the second end of wing portion 281A in their left hand by inserting their fingers through aperture 291 A and would grasp second end 290B of wing portion 281B by inserting their fingers through aperture 291B. The wearer would then move their arms in the directions indicated by the arrows in FIG. 14 in a generally outward, downward and sideways manner thereby forcing the contraction of the means for contraction composed of back panel 260 and wing portions 281A and 281B. In this way, compressive force would be generated in a generally inward direction. Of course, a cushion 15 could be disposed underneath wing portions 281A and 281B to modify the compressive force applied to the incision site. Similarly, a number of cushions 17 such as those illustrated in FIG. 8 may be detachably attached to the inside of the wing portions and back portion as necessary.

Figure 15:
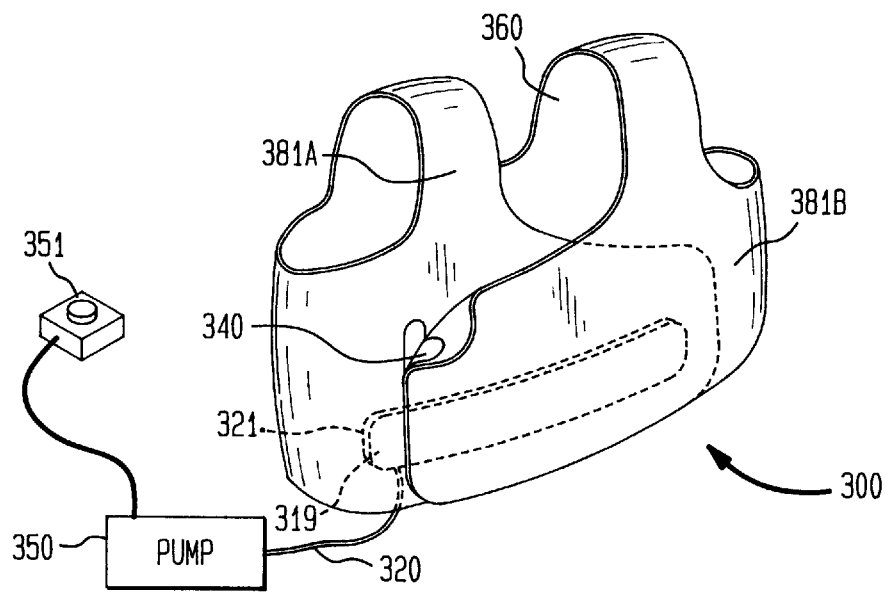
FIG. 15 is a perspective view of another version of the present invention.
Figure 16:
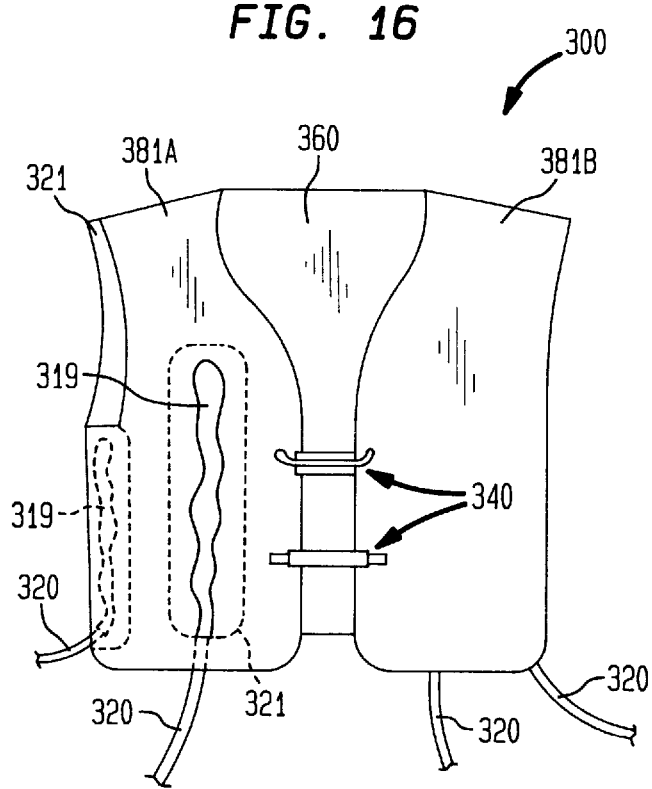
FIG. 16 is a perspective view of another version of the present invention.

Two related embodiments are illustrated in FIGS. 15 and 16. FIG. 15 illustrates a vest 300 very similar to that disclosed in FIG. 14. In this case, however, wing portion 381A and 381B are designed to overlap. In fact, they may be attached to each other through a fastener 340. This fastener may be a VELCRO® fastener, a convention hook, a plurality of strings to be tied together, or any other similar device. In this case, wing portion 381A includes a cavity 321 containing an inflatable bladder 319. Bladder 319 is in fluid or gas communication with a pump 350 via hose or conduit 320. The pump is in actuable contact with a device 351 which may be a switch, key, button or the like. In this instance, the operating means for actuating may be the device 351 and pump 350 which is engaged by the wearer just prior to or during a cough. When actuated, a signal is sent to the pump 350 wherein the pump 350 pumps fluid or gas through conduit 320 into inflatable bladder 319 whereupon it expands. Since wing portions 381B and 381A are releasably attached to one another, the outward expansion of the vest 300 is extremely limited. Instead, the vest will apply a constrictive action and a compressive force to the chest of the patient much like an inflatable blood pressure cuff. This provides the same sort of compressive force as previously discussed by the action of crossing the wing portions across the chest. The compressive force may be released by deactuating the device, switch or key. This may require depressing, for example, a separate button not shown, which forces the pump 350 to reverse its direction and withdraw the fluid or gas from the bladder 319. Alternatively, device 351 may be designed such that it needs to be depressed or engaged in order to maintain a positive pressure forcing material into inflatable bladder 319. As soon as the patient's finger is removed, the device will deflate. A hand pump also may be used.

This type of device is particularly useful in that it may be actuated effectively by people who have lost the use of one or both of their arms. In fact, this device may be linked to a pedal or to some other actuating device to accommodate quadriplegic and other handicapped patients.

FIG. 16 illustrates a similar device; however, the device illustrated in FIG. 16 more closely resembles a traditional vest. A plurality of cavities 321 are provided, each containing one or more bladders 319. It also should be noted that certain bladders contained within the vest 300 may be maintained at some minimum level of inflation at all times, whereby they may be used as a second means of modifying the compressive force applied to a portion of the torso and for adjusting the comfort or fit of the device. These bladders then may be additionally inflated to assist in providing compressive force throughout the entire circumference of the torso during a cough. These bladders 319 will be deflated, but not deflated completely. Therefore, even after deactuation, the device will provide the requisite cushioning or provide for a snug fit, without exerting a compressive force, unless re-actuated. The bladders 319 may be fully deflated as well.

Figure 17:
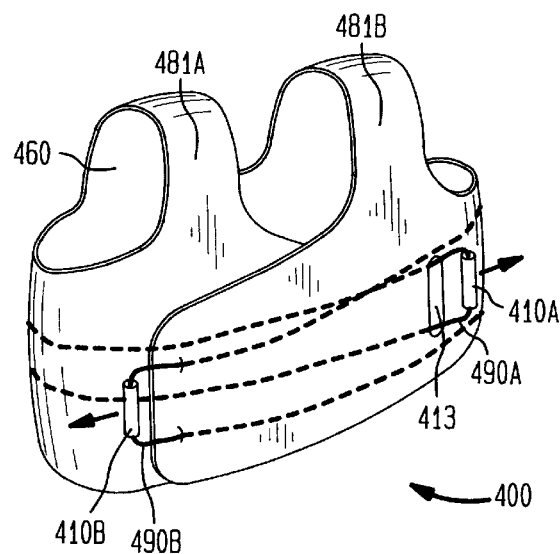
FIG. 17 is a perspective view of the device of FIG. 15 is showing a different compressive force means.

FIG. 17 is another embodiment of a vest style device in accordance with the present invention. In this embodiment, device 400 includes a back portion 460 and a plurality of wing portions 481A and 481B. Wing portion 481B also contains a slot 413 through which the second end 490A of wing portion 481A is threaded, such that it may be grasped from the outside of the vest. The second end of wing portion 490A is provided with a means for actuating/deactuating in the form of a handle 410A and a similar means for actuating/deactuating 410B is provided at the second end 490B of wing portion 481B. To apply compressive force before or during a cough, a patient wearing the vest would grasp handle 410A in their left hand and grasp handle 410B in their right hand and pull in an outward and generally sideways direction, as indicated by the arrows. Wing portion 481B would generally slide over top of wing portion 481A, except that a portion of wing portion 481A will be pulled through slot 413 as the device constricts. As with all other instances, this will apply a compressive force to the torso of a patient.

Figure 24:
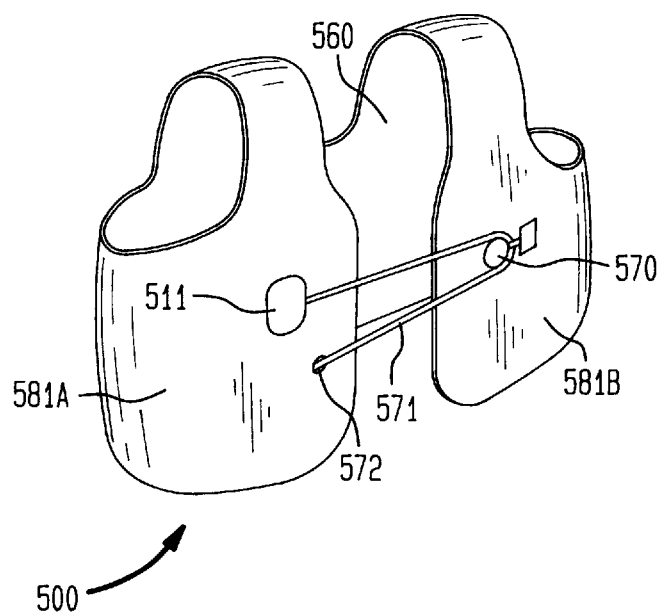
FIG. 24 is a perspective view of the device of FIG. 15 showing a variation of the compressive force means.

FIG. 24 illustrates yet another embodiment of the invention. In this case, a vest-styled device 500 is provided having a back portion 560, a front-right panel or front-right portion 581A and a front-left panel or front-left portion 581B. In this instance, the front-right panel 581A is also a wing portion 581A, and front-left panel 581B is a wing portion 581B. In the embodiment illustrated, a pulley 570 is attached to wing portion 581B and one end of a cord 571 is affixed at one to wing portion 581A through a rivet 572 or other retaining device. Any retaining device which can maintain the cord in intimate contact with wing 581A, such as a loop, an adhesive, or the like, may be used. Cord 571 is then threaded through pulley 570 and provided at its other end with an operating means for actuating, such as handle 511. This device is worn as any other vest described herein. However, prior to or during the onset of a cough, the patient merely grabs the operating means, i.e., handle 511, in their right hand and moves their right arm in an outward and generally sideways direction as previously described. This draws wing portions 581A and 581B closer together. In fact, preferably, these wing portions are designed such that, for example, wing portion 581A will slide over top of wing portion 581B to allow the wing portions to actually cross one another. In so doing, the vest is constricted and a compressive force is applied in a generally inward direction. This device is particularly advantageous as it may be actuated/deactuated with only one hand. A series of additional pulleys, not shown, could be provided and cord 571 could be extended such that, indeed, the device could be actuated by foot. Finally, by the use of one or more pulleys as described herein, the device could actually be hooked to a motor which would be actuated to cause the device to constrict or to release the compressive force on demand.

Figure 18:
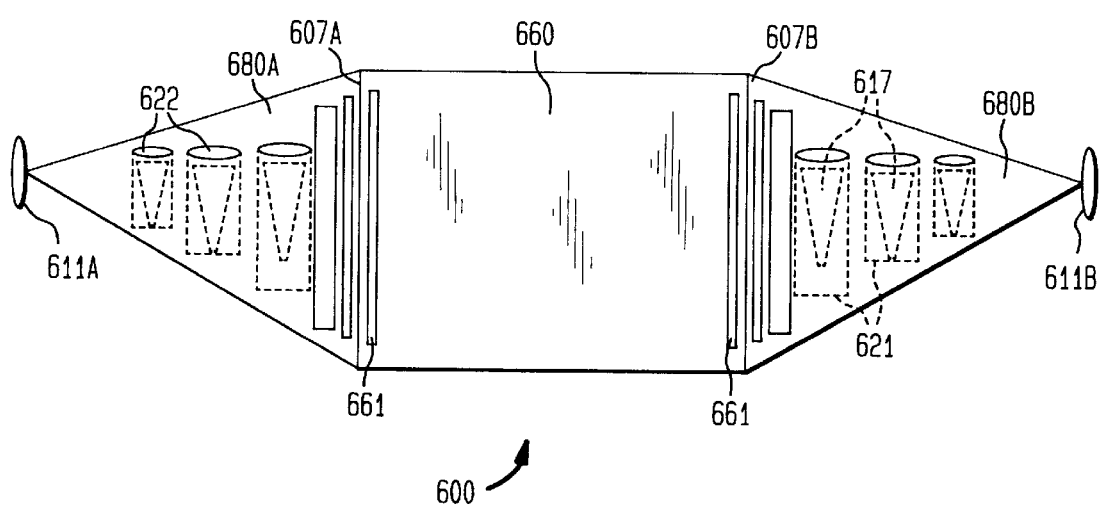
FIG. 18 is a top plan view of the device of FIG. 9 showing receptacles for receiving a front portion.
Figure 19:
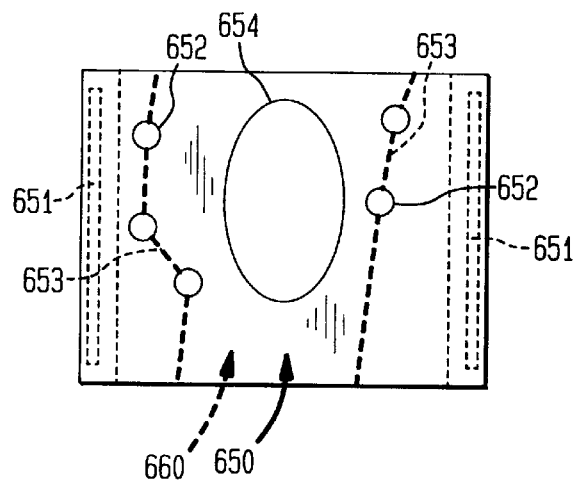
FIG. 19 is a top plan view of a first portion which is used in connection with the device of FIG. 18.

Another preferred embodiment in accordance with the present invention is illustrated in FIG. 18 as device 600. This device is identical to that described previously in FIG. 9 in that it includes a back panel portion 660 and attached wing portions 680A and 680B. These wing portions 680A and 680B each contain cavities 621 having openings 622 into which generally cone or wedged shaped cushions 617 can be placed. However, in addition to the foregoing, back portion 660 also includes two VELCRO fastening strips 661 located adjacent the first ends 607A and 607B of wing portions 680A and 680B, respectively. These VELCRO® strips are disposed to engage opposing VELCRO® strips located on the underside of a front panel or front position 650, illustrated in FIG. 19. Front panel 650 is removably attached to back panel 660 when VELCRO® strips 651 located on the underside thereof engage strips 661 on the back portion or back panel 660. A sleeve is thus formed. VELCRO® is but a preferred means of attaching the front portion 650 to the back portion 660. Any other releasable and reattachable means such as the use of snaps and reusable adhesives are also contemplated. Front portion 650 additionally includes apertures 652 through which catheters, monitors and the like may travel from a patient's torso to one or more devices. The pillow or cushion 654, useful for, for example, engaging the incision site to modify the compressive force applied thereto, may be integrally formed with front panel 650, as illustrated in FIG. 19. Alternatively, a pillow or cushion may be inserted on the patient's chest prior to attaching front portion 650 to back portion 660.

During an emergency, it may be necessary for a surgeon to gain immediate access to the incision site, if not to the torso. Therefore, front portion 650 is designed to be ripped away from back portion 660 when necessary. Perforations 653 also may be provided, which will facilitate ripping front portion 650 away from the body in a manner which will not tangle catheters, wires and the like which may have been fed therethrough.

Figure 20:
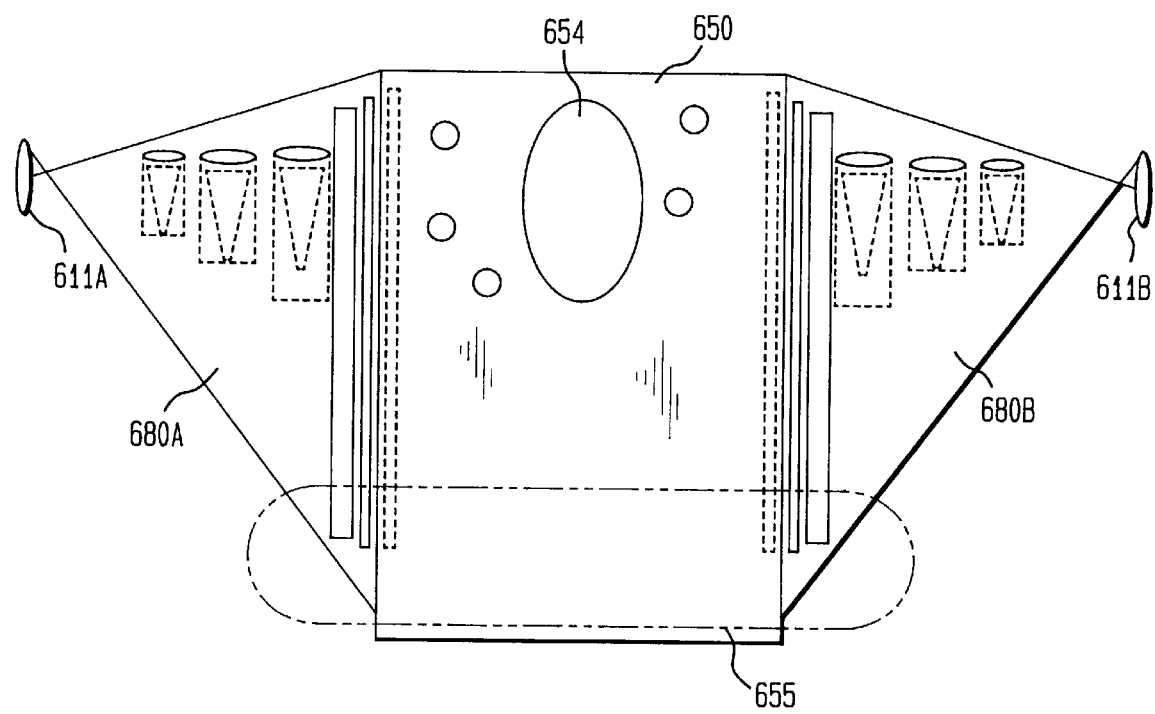
FIG. 20 is a top plan view of the device of FIG. 18 showing an extension therein and attached thereto.

Of course, it is possible to eliminate VELCRO® strips 661 by covering the entire inner surface with a fabric or material which may cooperate with VELCRO®, or other similar fastening devices to retain front portion 650 in combination therewith. In addition, it is not necessary that a front portion 650 be attached to back portion 660. Instead, the front portion 650 may attach to the inner surfaces of wing portions 680A and 680B, respectively. The combination of a front portion 650 and a back portion 660 to form a constrictive device in accordance with the present invention is illustrated in FIG. 20. FIG. 20 also illustrates an elongated region 655 which allows the constrictive device of the present invention to extend over substantially the entire torso, including the chest and abdomen of a patient, so as to provide compressive forces to the chest and/or the abdomen.

Figure 21:
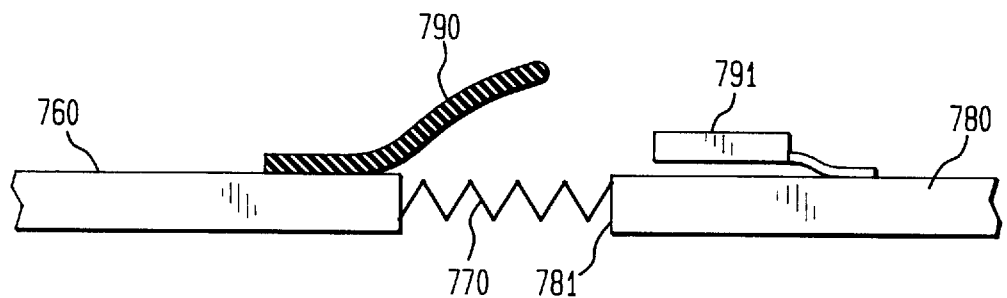
FIG. 21 is a bottom side elevation view of a device of the present invention showing an accordion-like member.
Figure 22:
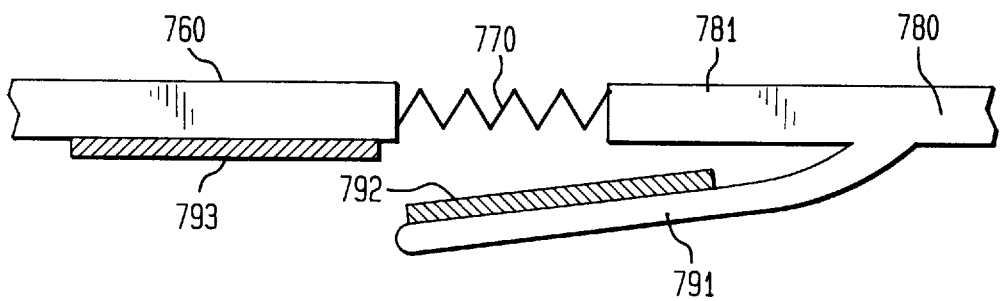
FIG. 22 is a bottom side elevation view of a variation of the member of FIG. 21.
Figure 23:
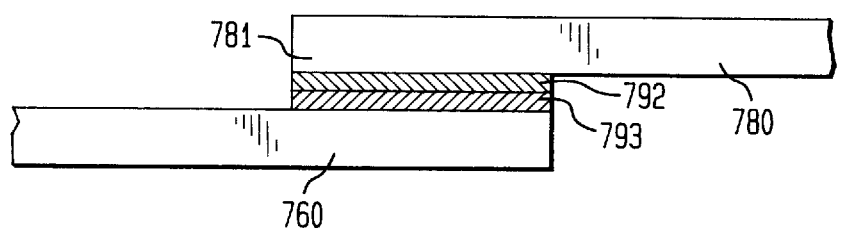
FIG. 23 is a bottom side elevation view of a variation of a device with interchangeable wings and back panels.

The devices of the present invention also may be designed such that it may accommodate a wide range of torso sizes. As shown in FIG. 21, a device including back portion 760 and, for example, a left wing portion 780, may be interconnected by an accordion or pleated member 770 which may be folded to a relatively smaller length or extended to accommodate a larger sized torso. In operation, strap 790 would be removed from buckle 791 and wing portion 780 moved away from back portion 760 until the proper dimension for the constrictive device is reached. Then, strap 790 would be threaded back through buckle 791 to fix the effective length of the wing portion. FIG. 22 illustrates an identical configuration. However, instead of a buckle and strap 790 and 791, respectively, a tab 791 is provided with a VELCRO® pad 792 designed to engage an opposing VELCRO® pad 793 on back portion 760. Finally, as illustrated in FIG. 23, back portion 760 can be provided with a VELCRO® pad 793 on its outer surface designed to engage a VELCRO® pad 792 disposed on the inner surface of wing portion 780 adjacent the first end 781 thereof. The wing portion is therefore removable relative to the back portion 760. This allows one to design a system where a plurality of different sized back panels and different sized wing panels may be used. Each of the various wing panels and back panels may be interchangeable. A strap member, not shown, may also be provided to ensure that the members do not pull apart during use.

Figure 25:
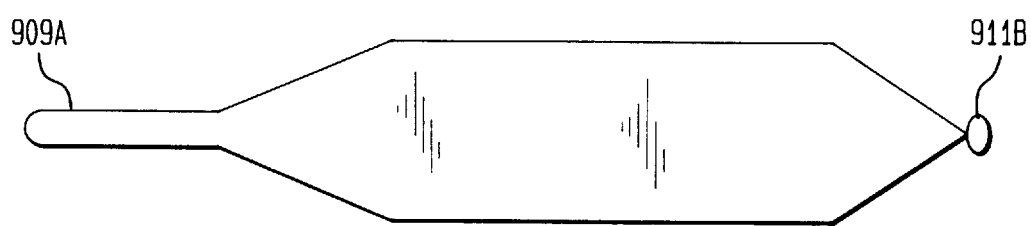
FIG. 25 is a top plan view of another version of the device of FIG. 1.

The devices of the present invention also may be designed as shown in FIG. 25 such that end portion 909A extends out in an elongated rectangular shape so as to fit through ring 911B. In this embodiment, the patient would insert the elongated end 909A into the ring 911B across the patient's affected area of the torso. The patient would then loop end 909A back over ring 911B and pull in the opposite direction from the direction in which the patient inserted the end 909A. For instance, from the patient's left to their right. This operation would be similar to tightening a belt such that when the patient pulls on the end 909A, the device creates the compressive force as described in the above embodiments. This particular embodiment may be varied by reversing the positions of the end piece and ring such that they are on opposite sides from those shown in FIG. 25.

In all of the embodiments discussed above, there is provided an area in which to display indicia. This indicia may include any written or pictorial information such as advertisements, instructions and the like which may be viewed by an observer whether or not the device is in operation. The area for providing indicia may be anywhere on the device including on the inside or outside of the back portion, the wings, the front portion or portions of the vest.

As these and other variations and combinations of the features described above can be used, the spirit and scope of the appended claims should not be limited to the description of the preferred versions contained herein.

What is claimed is:

1. A method for mitigating the pain experienced by a patient during coughs following surgery to at least one portion of the patient's torso and for increasing the effectiveness of the patient's coughs, comprising the steps of:

providing a means for constricting adapted to circumferentially surround at least one portion of the torso of the patient when actuated;

causing said means for constricting to constrict about at least one portion of the torso of the patient so as to apply a compressive force to the torso for restricting the expansion of at least one portion of the torso just prior to, or during a cough; and causing said means for constricting to release said compressive force from the at least one portion of the torso of the patient immediately following said cough and remain in a non-actuated position until the next actuaction.

2. The method of claim 1, wherein said means for constricting is arranged such that it is maintained in a position whereby it is immediately and repeatedly caused to constrict prior to or during successive coughs and immediately and repeatable released following successive coughs.

3. The method of claim 1, wherein said means of constricting includes a back portion and a plurality of wing portions, said wing portions each having a first end associated with said back portion and a second end disposed to be wrapped around at least a portion of the torso of the patient and wherein said means for constricting is caused to constrict about the torso of the patient by grasping said second ends of said wing portions and crossing them over torso.

4. The method of claim 2, wherein said means of constricting includes a back portion and a plurality of wing portions, said wing portions having a first end associated with said back portion and a second end disposed to be wrapped around at least a portion of the torso of the, said means for constricting also including a means for actuating and deactuating cooperating with said means for constricting adjacent said second ends of said wing portions and wherein said means for constricting is caused to constrict about the torso of the patient by grasping said means for actuating/deactuating and causing said plurality of wings to advance across the torso.

5. The method of claim 1, wherein at least a portion of said means for constricting is inflated causing said means for constricting to constrict about the torso of the patient so as to apply a compressive force to the torso just prior to, or during a cough.

6. The method of claim 1 further comprising the step of actuating said means for constricting such that it circumferentially surrounds the torso and engages a portion of the torso including an incision site.

7. The method of claim 6 further comprising the step of positioning a means for modifying the compressive force applied to an incision site so as to engage an incision site on the torso when said means for constricting is actuated.

* * * * *

UNITED STATES PATENT AND TRADEMARK OFFICE
CERTIFICATE OF CORRECTION

PATENT NO. : 5,843,008
DATED : December 1, 1998
INVENTOR(S) : Gerhard

It is certified that error appears in the above-identified patent and that said Letters Patent is hereby corrected as shown below:

In the Abstract, line 5, "wing portion" should read --wing portions--.

Figure 4C:
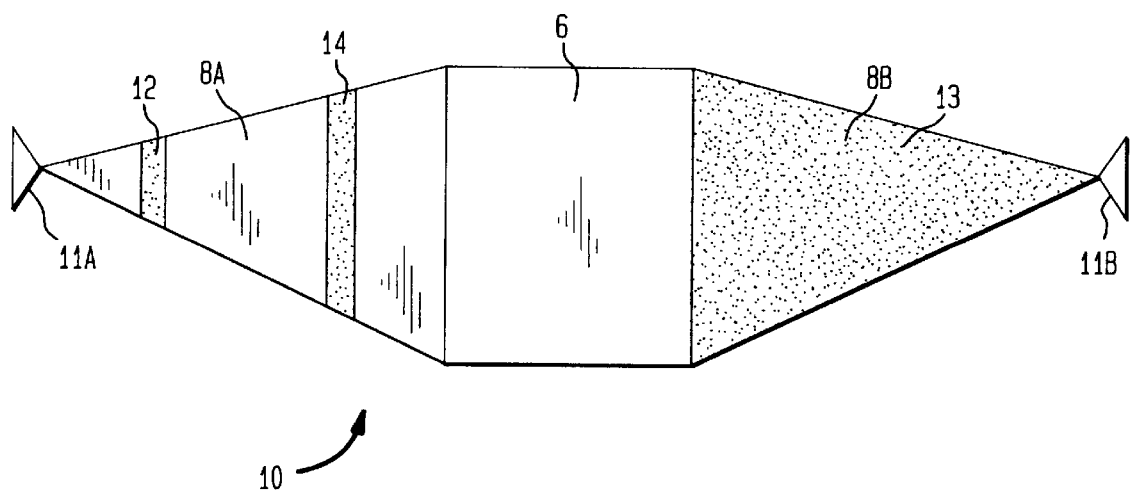

In the drawings, "FIG. 4C" should read --FIG. 5--.

Column 5, line 37, delete "is", second occurrence.

Column 9, line 7, "resent" should read --present--.

Column 10, line 19, delete "30".

Column 15, line 34, "repeatable" should read --repeatedly--.

Column 16, line 8, "over torso" should read --over the torso--.

Column 16, line 13, "the, said" should read --the patient, said--.

Column 16, lines 17, 18, "actuating/deactuating" should read --actuating and deactuating--.

Signed and Sealed this

Eighteenth Day of May, 1999

Attest:

Q. TODD DICKINSON

*Attesting Officer*  *Acting Commissioner of Patents and Trademarks*